(12) United States Patent
Aguirre, Jr. et al.

(10) Patent No.: US 10,881,421 B2
(45) Date of Patent: Jan. 5, 2021

(54) MECHANICAL END EFFECTOR

(71) Applicant: Technische Universiteit Delft, Delft (NL)

(72) Inventors: Milton Edward Aguirre, Jr., Delft (NL); Tim Horeman, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 571 days.

(21) Appl. No.: 15/483,245

(22) Filed: Apr. 10, 2017

(65) Prior Publication Data
US 2017/0281210 A1   Oct. 5, 2017

Related U.S. Application Data

(63) Continuation of application No. PCT/NL2015/050704, filed on Oct. 8, 2015.

(30) Foreign Application Priority Data

Oct. 8, 2014 (NL) .......................... 2013592
Dec. 15, 2014 (NL) .......................... 2013982

(51) Int. Cl.
*A61B 17/28* (2006.01)
*A61B 17/29* (2006.01)
(Continued)

(52) U.S. Cl.
CPC .......... *A61B 17/282* (2013.01); *A61B 17/285* (2013.01); *A61B 17/2841* (2013.01);
(Continued)

(58) Field of Classification Search
CPC . A61B 17/282; A61B 17/2841; A61B 17/285; A61B 17/29; A61B 2090/034;
(Continued)

(56) References Cited

U.S. PATENT DOCUMENTS

| 3,527,492 A | 9/1970 | Hollis | |
|---|---|---|---|
| 4,962,957 A * | 10/1990 | Traber | ...................... B25J 1/04 294/100 |

(Continued)

FOREIGN PATENT DOCUMENTS

| NL | 2009200 | 1/2014 |
|---|---|---|
| WO | 03/026519 | 4/2003 |
| WO | 2016/056908 | 4/2016 |

*Primary Examiner* — Erich G Herbermann
(74) *Attorney, Agent, or Firm* — Peacock Law P.C.; Justin Muehlmeyer

(57) ABSTRACT

A mechanical end effector comprising at least two movable parts, wherein each of the movable parts is mounted on at least two supports, wherein a relative position of the movable parts with respect to each other is variable by changing the relative position of the supports with respect to each other, and wherein the supports of the movable parts comprise bendable members, wherein the bendable members are equipped with mechanical properties that arrange for flexing of the bendable members when a force applied by the supports of the movable parts exceeds a predefined value and the bendable members are embodied as cooperating bands to arrange that flexing of the cooperating bands provides a visual feedback to a user.

5 Claims, 5 Drawing Sheets

(51) Int. Cl.
*A61B 17/285* (2006.01)
*A61B 90/00* (2016.01)
(52) U.S. Cl.
CPC ...... *A61B 17/29* (2013.01); *A61B 2017/2937* (2013.01); *A61B 2017/2941* (2013.01); *A61B 2090/034* (2016.02); *A61B 2090/064* (2016.02); *A61B 2090/0811* (2016.02)
(58) Field of Classification Search
CPC ...... A61B 2090/064; A61B 2090/0811; A61B 2017/2937; A61B 2017/2941
See application file for complete search history.

(56) References Cited

U.S. PATENT DOCUMENTS

2011/0288579 A1    11/2011  Hyodo
2015/0028613 A1*  1/2015  Nakayama ........... B25J 15/0206
                                                                294/196

* cited by examiner

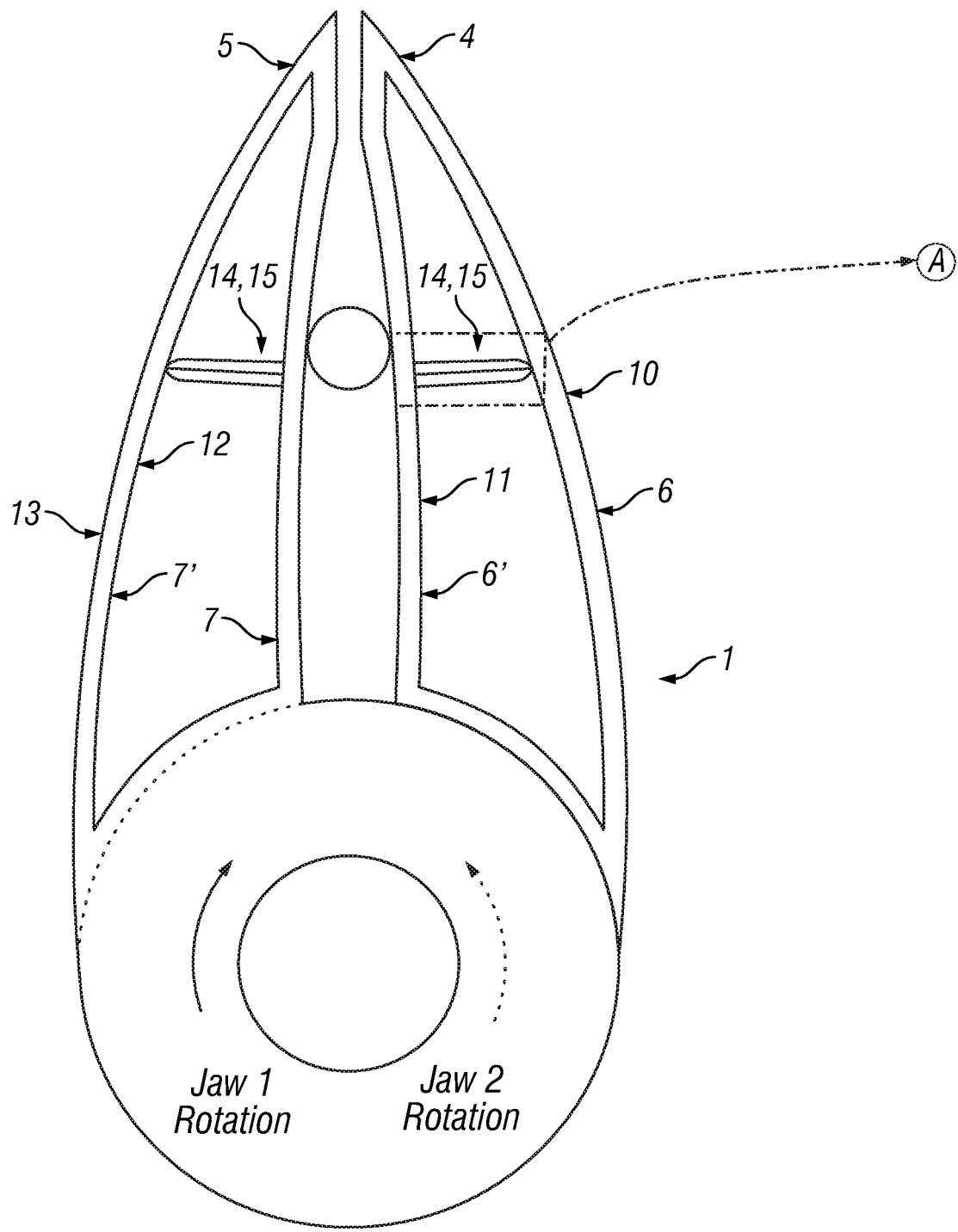
FIG. 5,A

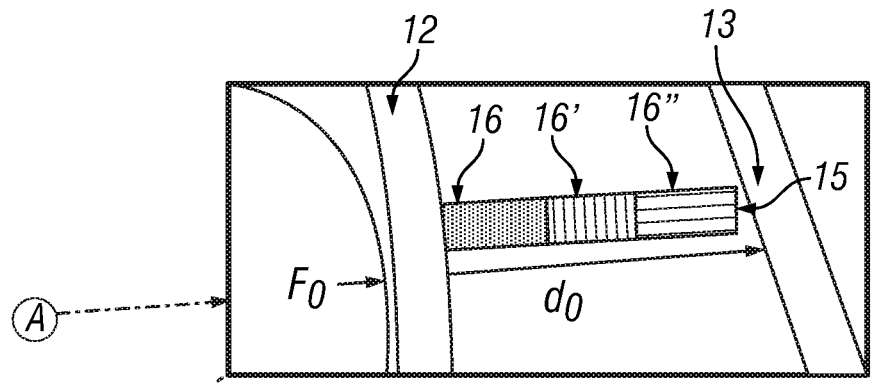
FIG. 5,B
$F_0 = 0\ N$
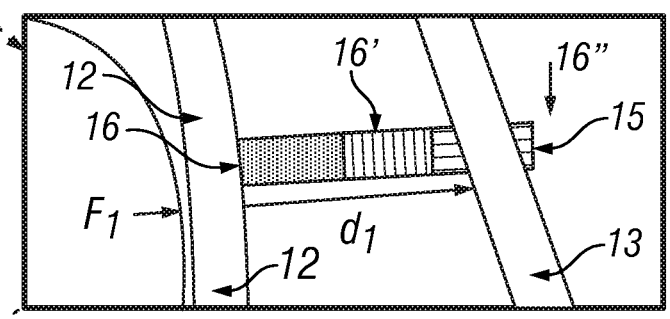
FIG. 5,C
$F_1 > F_0$
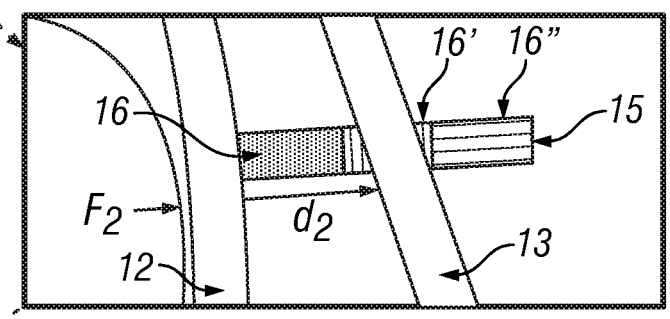
FIG. 5,D
$F_2 > F_1$
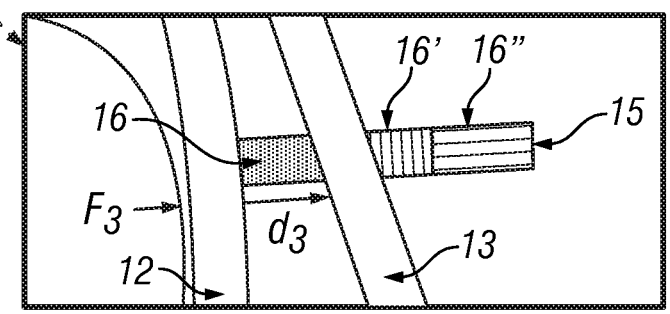
FIG. 5,E
$F_3 > F_2$

MECHANICAL END EFFECTOR

CROSS-REFERENCE TO RELATED APPLICATIONS

This application is a continuation application of Patent Cooperation Treaty Application No. PCT/NL2015/050704, filed on Oct. 8, 2015, which claims priority to Netherlands Patent Application No. 2013982, filed on Dec. 15, 2014, and Netherlands Patent Application No. 2013592, filed on Oct. 8, 2014, and the specifications and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to a mechanical end effector comprising at least two movable parts, wherein each of the movable parts is mounted on at least one support, wherein a relative position of the movable parts with respect to each other is variable by changing the relative position of the supports with respect to each other, and wherein the supports of the movable parts comprise bendable members. Usually the supports of the two movable parts share a common base or base structure.

Description of Related Art Including Information Disclosed Under 37 C.F.R. §§ 1.97 and 1.98

Such a mechanical end effector wherein each of the movable parts is mounted on two supports appears to be disclosed in FIG. 6 of WO03/026519, although this is far from certain considering the obscure discussion of this figure on page 6 of this citation's description. Considering that FIG. 6 of WO03/026519 bears resemblance with the figures that are attached hereto to elucidate the invention, it is assumed that particular features as provided in the preamble of the main claim are common to the invention and the prior art.

From U.S. Pat. No. 3,527,492 a trash pickup device is known which comprises two movable parts, wherein each of the movable parts is mounted on at least one support, wherein a relative position of the movable parts with respect to each other is variable by changing the relative position of the supports with respect to each other, and wherein the supports of the movable parts comprise bendable members that are equipped with mechanical properties that arrange for flexing of said members when a force applied by the supports of the movable parts exceeds a predefined value.

A mechanical end effector can for instance be embodied as a gripper or a cutter, and may be in use in robotics or surgical applications, particularly in minimal invasive surgery. One of the problems in using a mechanical end effector that is particularly bothersome in robotics and surgical applications is the lack of sensitivity of the effector in terms of forces that may be applied to an object. A further problem is its lacking capability to provide its user of feedback on the forces that are applied with the effector on an object which is to be manipulated or cut. This is particularly problematic in surgical applications.

BRIEF SUMMARY OF THE INVENTION

It is one of the objectives of the invention to provide a solution or at least an improvement regarding the problem of lacking feedback for the user.

The mechanical end effector of the invention is provided with one or more of the features according to the appended claims.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 5A shows a second embodiment of a mechanical end effector according to the invention, wherein FIGS. 5B-5E show details of visual feedback provided to the user when different amounts of force are exerted with the effector of FIG. 5A;

DETAILED DESCRIPTION OF THE INVENTION

Figure 1:
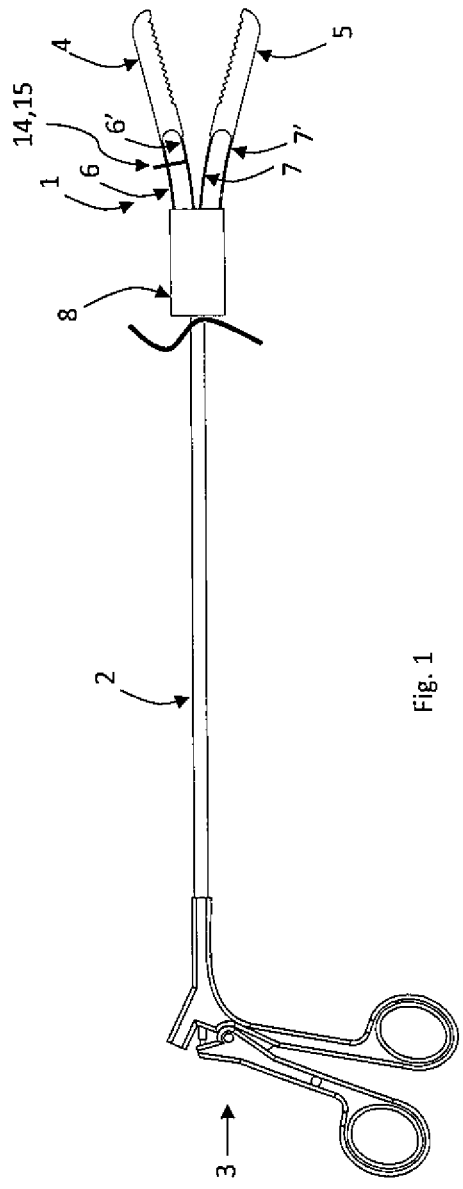
FIG. 1 shows a mechanical end effector according to a first embodiment of the invention.

In a first aspect of the invention the bendable members are arranged to flex and deform to an extent that is limited by a relative position of the cooperating bands with respect to each other, that restricts a room for bending of said pair of cooperating bands.

The said room between the cooperating bands is very instrumental in enabling suitable bending of at least one of the bands thus facilitating the ability to restrict or exceed a usual range of forces that may be applied with the movable parts on an object, and at the same time provide an effective means of visual and/or tactile feedback to a user that applies the forces to the movable parts. Interactions between the cooperating bands enable the usual range of forces to be restricted or exceeded through intentional con-tact of these bands. Exceeding or restricting a usual range of forces is valuable when performing particularly precise or robust tasks, such as manipulation of soft tissues and driving a suturing needle.

The mechanical end effector of the invention is preferably arranged such that each of the bendable members is embodied as a pair of cooperating bands predominately running parallel in an unloaded situation from a base or base structure to the movable part that the bands support, and that in a loaded situation the cooperating bands of each bendable member deform to an extent that is limited by a relative position of the cooperating bands with respect to each other, that restricts a room for bending of said pair of cooperating bands.

Suitably a further visual indicator or marker is provided on the cooperating bands that provide a visual feedback to a user when the cooperating bands are flexing. The visual feedback provides the user with reliable information on the amount of force which is applied to the object. The predefined value that initiates flexing of the bendable members can in connection therewith be suitably chosen within a range of usual forces that are applied when the effector is used for gripping or grasping an object safely and effectively.

In some embodiments it is preferred that the visual indicator or marker is embodied as a pillar or 'needle' gauge provided on one of the cooperating bands of the bendable members which enables measuring a deflection of the co-operating bands with respect to each other which thus provides a clear indicator of the applied force. This is however only one particular embodiment and this specific choice is not the only possibility according to the invention, but helpful to explain the merits of the invention.

The ease of handling and using the mechanical end effector of the invention is promoted by arranging that the pillar or needle gauge is provided with regions showing visually discriminate patterns.

In an embodiment wherein the mechanical end effector of the invention comprises at least two movable parts embodying a jaw, and each of the movable parts is mounted on an outer support and an inner support, which outer supports extend between the said movable parts and a tube, and which inner supports extend between the said movable parts and a rod, wherein the rod is positioned in the tube and the rod and tube are longitudinally movable with respect to each other to adjust a relative position of the outer supports with respect to the inner supports so as to correspondingly adjust a relative position of the movable parts mounted on said supports, and wherein the supports of the movable parts comprise flexural members between on one end the rod and tube, and on another end the two movable parts, said flexural members arrange that a force applied by the supports to the movable parts is limited to a value which is defined by mechanical properties of the flexural members. With this construction a user is also provided with haptic feedback on the forces that are applied with the mechanical end effector, as well as visual feedback regarding these forces due to bending out of the flexural members when the applied forces exceed the said predefined value defined by the mechanical properties of the flexural members. This is particularly beneficial when the mechanical end effector is used as a grasper in prosthetics, robotics or surgical applications, particularly in minimal invasive surgery. Haptic feedback is further provided once intentional contact between the flexural members is established.

It is found that with particular features the usefulness of the mechanical end effector of the invention can be further improved so that larger forces can be applied without sacrificing its capability to provide the user with haptic and visual feedback.

For that purpose it is preferred that the flexural members of the supports are provided with stiffening elements and/or changes in cross-sectional area (in particular thickenings) to provide for locally increased stiffness and rigidity of the flexural members. This effectively increases the possibility to apply larger forces with the mechanical end effector whilst maintaining its capability to provide visual and haptic feedback to the user.

It is preferred that there are plural stiffening elements and/or thickenings on the flexural members of the supports that are separated from each other by intermediate, in comparison with said stiffening elements and/or thickenings relatively flexible parts of the flexural members of the supports. The degree of rigidity versus flexibility of the flexural members can thus be easily tailored to the needs of the user in a particular application.

Preferably both the inner supports and the outer supports for the movable parts comprise flexural members upon which said stiffening elements and/or thickenings are provided. This provides benefits particularly in a further embodiment in which said stiffening elements and/or thickenings on any pair of an inner support and an outer support that support a movable part have cooperating teeth or interacting elements that contact or interlock with each other upon actuation of the grasper. The cooperating teeth or interacting elements further increase the amount of force that can be applied by the grasper of the invention, whilst the required flexibility is maintained.

Suitably actuation of the mechanical end effector is executed by an outer sheath wherein all supports of the movable parts are movable into and out of said sheath, wherein the outer sheath is longitudinally movable along all supports of the two movable parts between two positions, a first position in which the supports of the two movable parts are moved out of said sheath and released from restriction imposed by the outer sheath and in which the relative position of the two movable parts is determined only by the relative position of the supports, and a second position in which all supports of the two movable parts are moved in-to the sheath so as to restrict the relative position of said supports and to arrange that the position of the two movable parts is determined by the outer sheath only.

In quite a different embodiment of the mechanical end effector of the invention another solution is applied which is however based on the same general principle that the flexural members of the supports are provided with stiffening elements and/or thickenings to provide for locally increased stiffness and rigidity of the flexural members. In this embodiment the stiffening elements and/or thickenings are embodied as casings of and movable along the individual flexural members of the supports and positionable by an outer sheath, wherein in a first position of said sheath said casings exhibit a predefined yet variable amount of play between said casings, and wherein in a second position of said sheath play between the casings is avoided or counteracted.

The invention will hereinafter be further elucidated with reference to the drawing of an exemplary embodiment of an apparatus according to the invention that is not limiting as to the appended claims.

Whenever in the figures the same reference numerals are applied, these numerals refer to the same parts.

Making reference first to FIG. 1 the mechanical end effector of the invention is indicated with reference 1. This mechanical end effector 1 is for exemplary purposes mounted at a distal side of a rod 2 which has on its proximal side a handle 3 which may be used for opening and closing the mechanical end effector 1. The mechanical end effector 1 of this exemplary embodiment comprises two movable parts 4, 5. The movable part 4 is mounted on two cooperating supports 6, 6', whereas the movable part 5 is mounted on two other cooperating supports 7, 7'. The supports 6, 6', 7, 7' of the two movable parts 4, 5 further share a common base or base structure 8. It is remarked however that the invention is also applicable to a construction in which both the movable part 4 and the movable part 5 are each individually mounted on a single support. This is immediately clear to the skilled person and requires no further elucidation with reference to a drawing.

Figure 4:
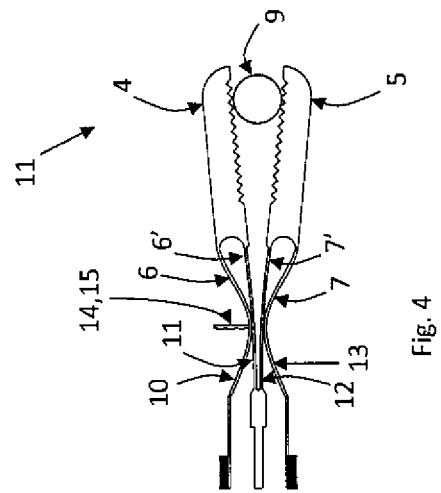
FIGS. 2, 3 and 4 show a sequence of events that occur when the mechanical end effector of FIG. 1 is used to grab an object.
Figure 3:
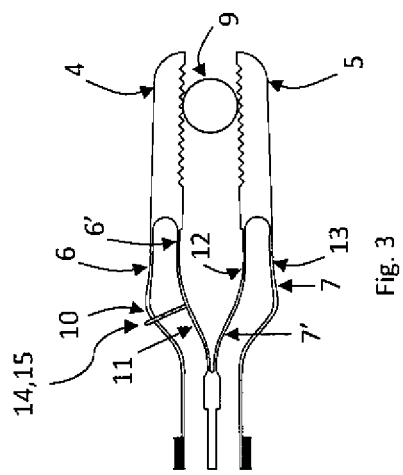
Figure 2:
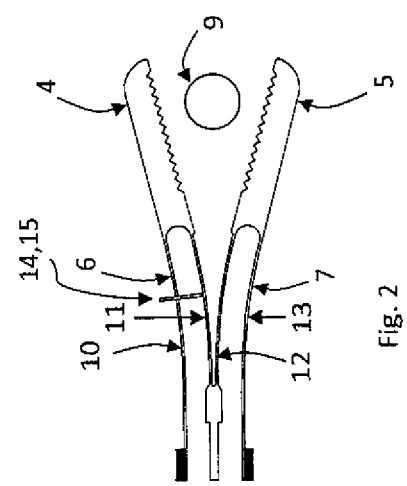

FIGS. 2, 3, and 4 show in detail the mechanical end effector 1 shown in FIG. 1 when the effector is used to grasp an object 9.

FIG. 2 shows the situation that the mechanical end effector 1 is in the vicinity of the object 9 which is intended to be grabbed by the mechanical end effector 1. To enable this the mechanical end effector 1 is construed such that a relative position of the movable parts 4, 5 with respect to each other is variable. Movement of movable part 4 is done by changing the relative position of the supports 6, 6' of movable part 4 with respect to each other. Movement of movable part 5 is done by changing the relative position of the supports 7, 7' of movable part 5 with respect to each other.

The supports 6, 6' and 7, 7' of the movable parts 4, 5 comprise or are embodied as bendable members. The bendable members are equipped with mechanical properties that arrange for flexing of the bendable members when a force applied by the supports 6, 6' and 7, 7' of the movable parts 4, 5 exceeds a predefined value. The flexing of the bendable members can beneficially be used to provide a visual feedback to a user as will be explained hereafter.

The flexing of the bendable members arranges that when the movable parts 4, 5 engage the object 9 as shown in FIG. 3, a certain degree of deformation occurs of each of the bendable members embodying the supports 6, 6' and 7, 7'. By further increasing the actuation forces applied to the supports 6, 6' and 7, 7' eventually the situation emerges as shown in FIG. 4. Here the largest degree of deformation of the bendable members embodying the supports 6, 6' and 7, 7' is depicted.

One of the advantages of arranging that the supports 6, 6' and 7, 7' of the movable parts 4, 5 comprise or are embodied as bendable members is that a force applied by the supports 6, 6' and 7, 7' to the movable parts 4, 5 is limited to a well-defined pre-established value which is determined by properly selecting the mechanical properties of the bendable members. The contact of the bendable members acts as a mechanical end-stop that restricts (translational) motion of the actuation member and thus restricts larger applied forces. This exemplary embodiment is very suited when gripping soft tissue, as manipulating the tissue must be done without dangerously high forces.

In the exemplary first embodiment of the mechanical end effector of the invention as depicted in FIGS. 1-4, each of the bendable members is embodied as a pair of co-operating bands 10, 11 and 12, 13, which can provide visual feedback to a user. Additionally an indicator 14 or marker can assist to provide visual feedback with flexing of the cooperating bands 10, 11; 12, 13. The visual indicator 14 or marker is preferably embodied as a pillar or needle gauge 15, provided in this exemplary embodiment on one of the co-operating bands, in particular on the band 11 of the bendable members. This is however not essential; also one of the other bands 10, 12 or 13 could be selected as support for the pillar or needle gauge. It is also possible that only the relative position of the cooperating bands 10, 11; 12, 13 are used for providing visual feedback, or that another means of visual feedback is applied. The pillar or needle gauge 15 is one example of enabling easily measuring a deflection of the cooperating bands 10, 11 with respect to each other.

FIG. 5A shows a second embodiment of a mechanical end effector of the invention, wherein the instrument has two movable parts 4, 5, wherein each of the movable parts 4 resp. 5 is mounted on at least one support 6, 6' resp. 7, 7', and wherein a relative position of the movable parts 4, 5 with respect to each other is variable by changing the relative position of the supports 6, 6'; 7, 7' with respect to each other. This is in this second embodiment done by rotating of the supports 6, 6' and the supports 7, 7' with respect to each other.

Also in this second embodiment the supports 6, 6'; 7, 7' of the movable parts 4, 5 comprise bendable members embodied as cooperating bands 10, 11; 12, 13 that are equipped with mechanical properties that arrange for flexing of said members when a force applied by the supports 6, 6'; 7, 7' of the movable parts 4, 5 exceeds a predetermined value. In this case, the contact between the bendable members stiffens the individual jaw parts 4, 5. Thus further (rotational) actuation will generate larger forces that exceed the gripper's 'usual force range'. This embodiment can for instance be suitably applied when grasping a suturing needle. The contact between the jaw parts 4, 5 gives the user indication that sufficient force is being used for suturing with a needle.

The second embodiment of the mechanical end effector 1 shown in FIG. 5A can also be provided with an additional visual indicator 14 or marker to arrange that flexing of the cooperating bands 10, 11; 12, 13 provides a visual feedback to a user that is reproducible. The visual indicator 14 or marker is also in this embodiment provided as a pillar or needle gauge 15 mounted in this second exemplary embodiment on both bands 11 and 12 of the bendable members.

FIGS. 5B-5E show in detail the deflection of the cooperating bands 12, 13 with respect to each other when an increasing amount of force is applied going from FIG. 5B to FIG. 5E. These figures further show that suitably the pillar or needle gauge 15 is provided with regions showing visually discriminate patterns 16, 16', 16" providing a very clear indication of the amount of the applied force by comparing the location of the position of the band 13 with respect to the discriminate patterns 16, 16', 16" on the pillar or needle gauge 15 that is mounted on the band 12.

Turning back now to the first embodiment of the mechanical end effector of the invention depicted in FIGS. 1-4, FIG. 2 shows the unloaded situation of the mechanical end effector 1 wherein the cooperating bands 10, 11 and 12, 13 predominantly run parallel from the base or base structure 8 to the movable part 4, 5 that the bands support. FIGS. 3 and 4 then show that in a loaded situation the cooperating bands 10, 11; 12, 13 of each bendable member deform to an extent that is limited by a relative position of the cooperating bands 10, 11; 12, 13 which eventually restricts a room for bending of said pair of cooperating bands 10, 11; 12, 13. This is clearly illustrated in FIG. 4.

Figure 6:
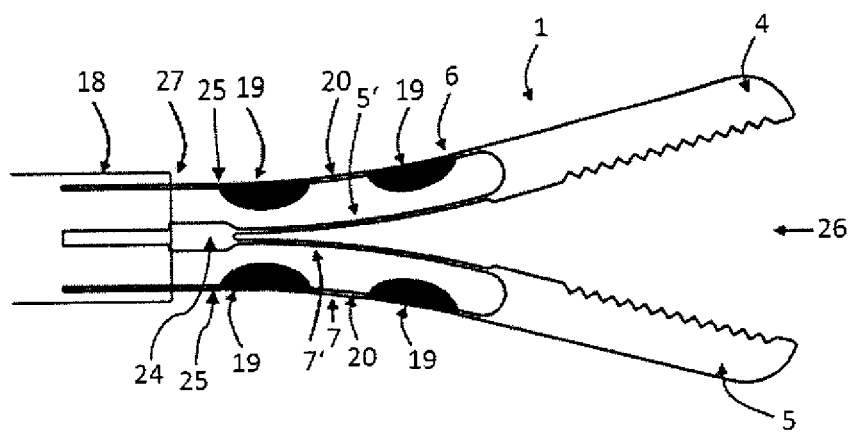
FIG. 6 shows a third embodiment of a grasper of the invention with an outer sheath retracted.
Figure 7:
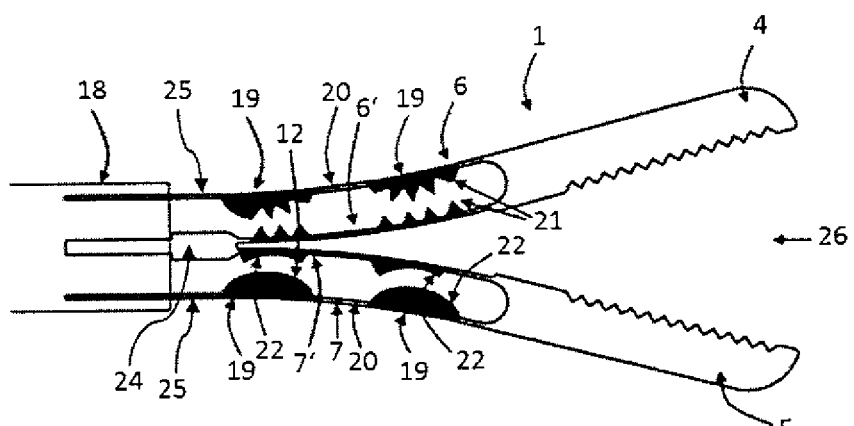
FIG. 7 shows a fourth embodiment of a grasper with the outer sheath retracted.

In the third and fourth embodiment shown in FIG. 6 and FIG. 7 the end effector 1 of the invention is embodied as a grasper comprises two movable parts 4, 5 defining a jaw 26. The movable part 4 is mounted on an outer support 6 and an inner support 6' cooperating with the outer support 6, whereas the movable part 5 is mounted on an outer support 7 and an inner support 7' that cooperates with the outer support 7.

The outer supports 6, 7 extend between the movable parts 4, 5 and a tube 25, whereas the inner supports 6', 7' extend between the said movable parts 4, 5 and a central rod 24 wherein the rod 24 is centrally positioned in the tube 25. The rod 24 and tube 25 are longitudinally movable with respect to each other to adjust a relative position of the outer supports 6, 7 with respect to the inner supports 6', 7' so as to correspondingly adjust a relative position of the movable parts 4, 5.

Opposite to the jaw 26 is the proximal side 27 of the grasper 1 at which side the grasper is controlled. At this proximal side 27 an outer sheath 18 is provided. For clarity purposes the outer sheath 18 is shown in a position in which the two movable parts 4, 5 of the jaw 26 are re-leased from restriction by this outer sheath 18 so as to enable that the relative position of the movable parts 4, 5 is exclusively determined by the relative position of the sup-ports 6, 6' and 7, 7'.

Operation of the grasper 1 with the outer sheath 18 in the retracted position is as follows. Movement of movable part 4 can be done by changing the relative position of the outer support 6 and inner support 6' of movable part 4 with respect to each other by appropriately longitudinally displacing the central rod 24 and tube 25 with respect to each other. Movement of movable part 5 can likewise be done by changing the relative position of the outer support 7 and inner support 7' of movable part 5 with respect to each other, in the same way by appropriately longitudinally displacing the central rod 24 and tube 25 with respect to each other.

In FIG. 6 and FIG. 7 the movable parts 4, 5 of the jaw 26 are moved concertedly by movement of the central supports 6' and 7' whilst the outer supports 6 and 7 remain stationary by keeping the tube 25 stationary and moving the central rod 24. Alternatively it is also possible that the movable parts 4, 5 of the jaw 2 are moved concertedly by movement of the outer supports 6 and 7 whilst the central supports 6' and 7' remain stationary by keeping the central rod 24 stationary and moving the tube 25.

In both situations shown in FIGS. 6 and 7 the outer sheath 18 is kept in a first position in which the two movable parts 4, 5 are released from any restriction imposed by the outer sheath 18 so that the relative position of the two movable parts 4, 5 is determined by the relative position of the supports 6, 6'; 7, 7' only. This corresponds to fine or delicate grasping.

When the outer sheath 18 is moved forward to engage the outer supports 6, 7 of the movable parts 4, 5 of the jaw 2, movement of said movable parts 4, 5 is restricted and the opening and closing of the jaw 2 is controlled by positioning and moving the outer sheath 18 back-and-forth. This corresponds to coarse or firm grasping. To be precise this functionality is realized by arranging that all supports 6, 6'; 7, 7' of the movable parts 4, 5 are movable into and out of said sheath 18, wherein the outer sheath 18 is longitudinally movable along all supports of the two movable parts 4, 5 between two positions, a first position in which the supports 6, 6'; 7, 7' of the two movable parts 4, 5 are moved out of said sheath 18 and released from restriction imposed by the outer sheath 18 and in which the relative position of the two movable parts 4, 5 is determined only by the relative position of the supports 6, 6'; 7, 7', and a second position in which all supports 6, 6'; 7, 7' of the two movable parts 4, 5 are moved into the sheath 18 so as to restrict the relative position of said supports 6, 6'; 7, 7' and to arrange that the position of the two movable parts 4, 5 is determined by the outer sheath 18 only.

It is remarked that the supports 6, 6' and 7, 7' of the movable parts 4, 5 comprise or are embodied as flexural members extending between on one end the rod 24 and tube 25 and on another end the two movable parts 4, 5. One of the advantages of arranging that the supports 6, 6' and 7, 7' of the movable parts 4, 5 comprise or are embodied as flexural members is that a force applied by the supports 6, 6' and 7, 7' to the movable parts 4, 5 is limited to a well-defined pre-established value which is determined by properly selecting the mechanical properties of the flexural members. It will be clear that this only applies when the outer sheath 18 is in the retracted position, when the position of the movable parts 4, 5 is only determined by the position of their respective supports 6, 6' and 7, 7'.

According to the invention the flexural members of the supports 6, 6'; 7, 7' extending between the rod 24 and tube 25 on one end, and on another end the two movable parts 4, 5 are provided with stiffening elements and/or thickenings 19 to provide for locally increased stiffness and rigidity of the flexural members in comparison with the remainder of said flexural members. FIG. 6 shows that there are plural stiffening elements and/or thickenings 19 which are provided only on the flexural members of the outer supports 6, 7. The rigidity of the inner supports 6', 7' is not particularly increased. These stiffening elements and/or thickenings 19 are separated from each other by intermediate, in comparison with said stiffening elements and/or thickenings 19 relatively flexible parts 20 of the flexural members of the supports 6, 7 to maintain a defined flexibility of the supports 6, 7.

In the embodiment of FIG. 7 the flexural members of both the inner supports 6', 7' and the outer supports 6, 7 are provided with said stiffening elements and/or thickenings 19. FIG. 7 further shows that said stiffening elements and/or thickenings 19 on any pair 6, 6'; 7, 7' of an inner support 6', 7' and an outer support 6, 7 that support a movable part 4, 5 have cooperating teeth 21 (on the sur-face of the thickenings 19 on supports 6, 6') or interacting elements (roughenings) 12 (on the surface of the thickenings 19 on supports 7, 7') that are capable to contact or inter-lock with each other upon actuation of the grasper 1. Such actuation is then done by moving the outer sheath 18 forward to restrict movement of the two movable parts 4, 5 and to position the grasper in the 'coarse' or 'firm' grasping mode of operation in the manner as explained here-above. Preferably the outer sheath 8 has an inner rectangular opening fit-ting to the supports 6, 6'; 7, 7' of the movable parts 4, 5. This provides additional stiffness against torsional/twisting loads.

The interlocking or contacting teeth 21 or roughenings 22 provided on the outer and inner supports 6, 6' and 7, 7' then further support and increase the amount of force that can be applied with the grasper of the invention. This is not further shown in the drawing considering that the manner in which this operates is perfectly clear for the skilled person. There is therefore no need for a further elucidation with reference to the drawing without compromising the skilled person's capability to work within the scope of the invention.

Figure 8:
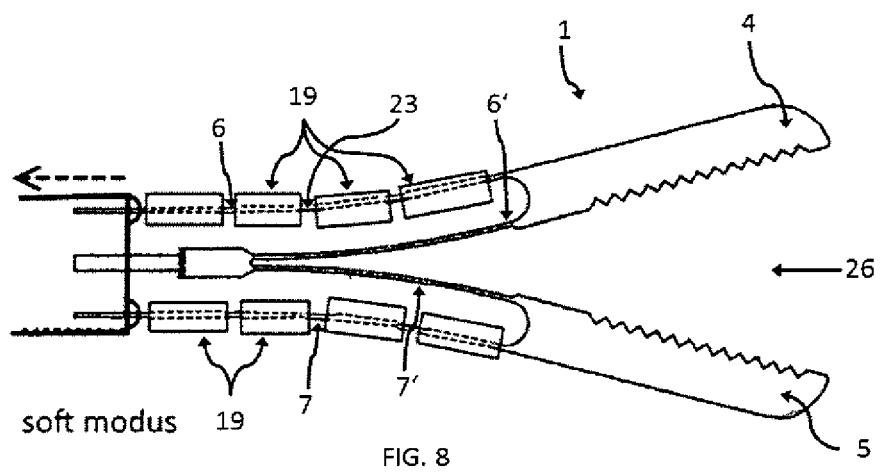
FIG. 8 shows a fifth embodiment of the grasper of the invention with an outer sheath retracted.
Figure 9:
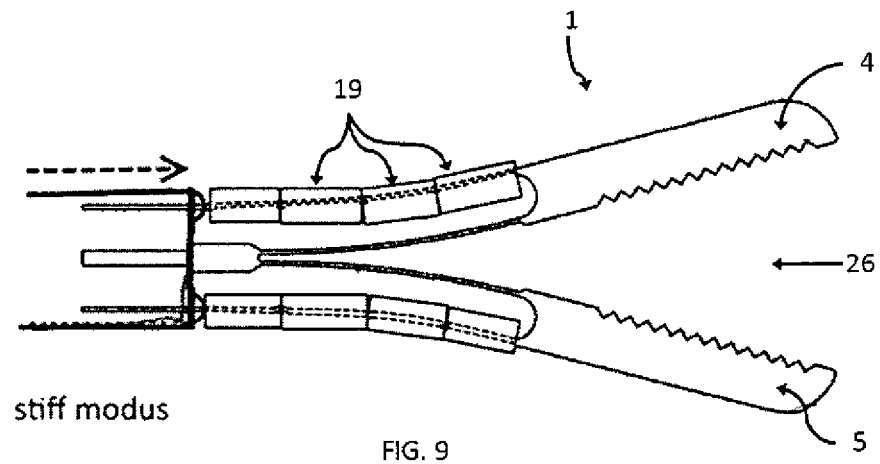
FIG. 9 shows the fifth embodiment of FIG. 8 wherein the outer sheath is moved forward.

FIGS. 8 and 9 relate to a fifth embodiment of the grasper 1 of the invention, which has the feature that the stiffening elements and/or thickenings are embodied as casings 19 movable along the individual flexural members of the supports 6, 7. These casings 19 are positionable by an outer sheath 18 which can assume two separate positions. FIG. 8 depicts a first position in which said sheath 18 is retracted and consequently said casings 19 exhibit a predefined yet variable amount of play 13 between said casings 19. This results in a relatively limited amount of force that can be applied with the movable parts 4, 5 that constitute the jaw 26 of the grasper. In a second and forwardly moved position of said sheath 18 as depicted in FIG. 9, play between the casings 19 is avoided or counteracted, and consequently flexibility of the flexural members of the supports 6, 7 is restricted. In this position relatively higher forces can be applied with the movable parts 4, 5 constituting the jaw of the grasper.

Although the invention has been discussed in the foregoing with reference to an exemplary embodiment of the mechanical end effector of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be re-solved using this exemplary embodiment.

What is claimed is:

1. A mechanical end effector, comprising: at least two movable parts selectively movable relative to one another between an unloaded position, a first load position and a maximum load position; a first pair of supports extending from a first one of said movable parts to a base, said first pair of supports selectively movable relative to one another between said unloaded, first bad and maximum bad positions to move said associated first movable part; a second pair of supports extending from a second one of said movable parts to said base, said second pair of supports selectively movable relative to one another between said unloaded, first load and maximum load positions to move said associated second movable part; each of said first and second pair of supports comprising a first end at a respective one of said movable parts, a second end at said base, a contact point located a distance apart from each of said base and said respective one of said movable parts, and comprising mechanical properties that: (i) permit selective flexing and deformation of said first and second pair of supports relative to the other said support in said respective pair of supports, and corresponding movement of respective ones of said moveable parts, upon application of force to said first and second pair of supports up to a predefined threshold value being sufficient to initiate contact at said contact point between supports in each of said pair of supports, and (ii) limit further displacement of said first and second pair of supports and increased force applied by said first and second pair of supports to respective ones of said movable parts beyond said contact point upon application of force exceeding said predefined threshold value at said second ends; wherein said unloaded position is defined by said first and second pair of supports in each of said first and second pair of supports being unflexed and predominantly parallel to one another between said base and said respective movable part, and said movable parts being spaced apart from one another; wherein said first load position is defined by at least one of said supports in each of said first and second pair of supports being flexed and deformed to a first angular relationship while spaced apart relative to the other support in each of said pair of supports sufficient to apply force to said respective movable part below said predefined threshold value and move said respective movable part to engage an object between said movable parts; wherein said maximum load position is defined by said at least one of said supports in each of said pair of first and second supports being flexed and deformed to a second angular relationship relative to and contacting the other support in each of said pair of first and second supports at said contact point upon application of force meeting said predefined threshold value, said contact point limiting further application of force applied to said first and second pair of supports at said second ends from being transferred beyond said contact point to said movable parts once contact is achieved, wherein a relative position of said supports of each of said pair of first and second pair of supports provides haptic feedback to a user of the force that is applied to said movable parts and wherein contact initiated at said contact point upon reaching said predefined threshold value of force provides haptic feedback to the user specific to and indicative of contact initiated at said contact point.

2. The mechanical end effector according to claim 1, wherein a relative position of said supports of each of said first and second pair of supports provides visual feedback to the user of the force that is applied to said movable parts.

3. The mechanical end effector according to claim 1, additionally comprising at least one of a visual indicator and marker provided on said first and second pair of supports that provide a visual feedback to the user with flexing of said first and second pair of supports.

4. The mechanical end effector according to claim 3, wherein at least one of said visual indicator and said marker is one of a pillar and a needle gauge, and is provided on one of said first and second pair of supports and, enables measuring a deflection of said first and second pair of supports within each of said pair of supports with respect to each other.

5. The mechanical end effector according to claim 3, wherein said pillar and said needle gauge is provided with regions showing visually discriminate patterns.

\* \* \* \* \*